United States Patent [19]
Smeltzer

[11] Patent Number: 5,789,171
[45] Date of Patent: Aug. 4, 1998

[54] **USE OF CNA, FNBA, FNBB, AND HLB, GENE PROBES FOR THE STRAIN-SPECIFIC IDENTIFICATION OF *STAPHYLOCOCCUS AUREUS***

[75] Inventor: Mark S. Smeltzer, Bryant, Ark.

[73] Assignee: Board of Trustees of the University of Arkansas, Little Rock, Ark.

[21] Appl. No.: 667,079

[22] Filed: Jun. 20, 1996

[51] Int. Cl.$^6$ .............................. C12Q 1/70; C07H 21/04
[52] U.S. Cl. .......................... 435/6; 435/810; 536/24.32; 935/6; 935/77; 935/78
[58] Field of Search ............................ 435/6, 91.2, 5, 435/810; 935/6, 77, 78; 536/23.1, 23.72, 24.33, 24.32

[56] References Cited

PUBLICATIONS

Minhas et. al J. Med. Microbiol. 42:96–101 (Feb. 1995).
Monzon–Moreno et. al. J. Med. Microbiol. 35:80–88 (Aug. 1991).

*Primary Examiner*—W. Gary Jones
*Assistant Examiner*—Debra Shoemaker
*Attorney, Agent, or Firm*—Benjamin Aaron Adler

[57] ABSTRACT

The present invention provides a method of clinically differentiating the presence of *Staphylococcus aureus* in isolated samples, comprising the step of: analyzing the hybridization profile observed in Southern blots utilizing DNA probes for genes selected from the group consisting of the cna gene, the fnbA gene, the fnbB gene, the hlb gene, the cna-up gene, the pcp gene, the pcp12 gene and the pcp34 gene. Also provided is a kit for clinically differentiating the presence of *Staphylococcus aureus* in isolated samples, comprising: (1) restriction enzymes to digest genomic DNA contained in said samples; and (2) DNA probes for genes selected from the group consisting of the cna gene, the fnbA gene, the fnbB gene, the hlb gene, the cna-up gene, the pcp gene, the pcp12 gene and the pcp34 gene.

10 Claims, 7 Drawing Sheets

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 23
        ( B ) TYPE: nucleic acid
        ( C ) STRANDEDNESS: double
        ( D ) TOPOLOGY: linear ( i i ) MOLECULE TYPE:
        ( A ) DESCRIPTION: other nucleic acid ( i i i ) HYPOTHETICAL: No ( i v ) ANTI-SENSE: No ( v i ) ORIGINAL SOURCE:

(B) STRAIN:
                    (C) INDIVIDUAL ISOLATE:
                    (D) DEVELOPMENTAL STAGE:
                    (F) TISSUE TYPE:
                    (G) CELL TYPE:
                    (H) CELL LINE:

(x i) SEQUENCE DESCRIPTION: SEQ ID NO:1:

ATGCACTTGT ATTCGTTATA CTG                                                                23

(2) INFORMATION FOR SEQ ID NO:2:

(i) SEQUENCE CHARACTERISTICS:
                    (A) LENGTH: 24
                    (B) TYPE: nucleic acid
                    (C) STRANDEDNESS: single
                    (D) TOPOLOGY: linear (i i) MOLECULE TYPE:
                    (A) DESCRIPTION: other nucleic acid (i i i) HYPOTHETICAL: No (i v) ANTI-SENSE: No (v i) ORIGINAL SOURCE:
                    (B) STRAIN:
                    (C) INDIVIDUAL ISOLATE:
                    (D) DEVELOPMENTAL STAGE:
                    (F) TISSUE TYPE:
                    (G) CELL TYPE:
                    (H) CELL LINE:

(x i) SEQUENCE DESCRIPTION: SEQ ID NO:2:

AGGCCACTCT TAGTCTGCTT ACAT                                                               24

(2) INFORMATION FOR SEQ ID NO:3:

(i) SEQUENCE CHARACTERISTICS:
                    (A) LENGTH: 30
                    (B) TYPE: nucleic acid
                    (C) STRANDEDNESS: single
                    (D) TOPOLOGY: linear (i i) MOLECULE TYPE:
                    (A) DESCRIPTION: other nucleic acid (i i i) HYPOTHETICAL: No (i v) ANTI-SENSE: No (v i) ORIGINAL SOURCE:
                    (B) STRAIN:
                    (C) INDIVIDUAL ISOLATE:
                    (D) DEVELOPMENTAL STAGE:
                    (F) TISSUE TYPE:
                    (G) CELL TYPE:
                    (H) CELL LINE:

(x i) SEQUENCE DESCRIPTION: SEQ ID NO:3:

ATCTTAGAGC TCACTTTTCA TTAACTCGCT                                                         30

(2) INFORMATION FOR SEQ ID NO:4:

(i) SEQUENCE CHARACTERISTICS:
                    (A) LENGTH: 30
                    (B) TYPE: nucleic acid
                    (C) STRANDEDNESS: single
                    (D) TOPOLOGY: linear (i i) MOLECULE TYPE:
                    (A) DESCRIPTION: other nucleic acid (i i i) HYPOTHETICAL: No ( i v ) ANTI-SENSE: No ( v i ) ORIGINAL SOURCE:
  ( B ) STRAIN:
  ( C ) INDIVIDUAL ISOLATE:
  ( D ) DEVELOPMENTAL STAGE:
  ( F ) TISSUE TYPE:
  ( G ) CELL TYPE:
  ( H ) CELL LINE:

( x i ) SEQUENCE DESCRIPTION: SEQ ID NO:4:

AATTTCCTAG GGCTCGACTG GTCCTTCTGC    30

( 2 ) INFORMATION FOR SEQ ID NO:5:

( i ) SEQUENCE CHARACTERISTICS:
    ( A ) LENGTH: 33
    ( B ) TYPE: nucleic acid
    ( C ) STRANDEDNESS: single
    ( D ) TOPOLOGY: linear ( i i ) MOLECULE TYPE:
    ( A ) DESCRIPTION: other nucleic acid ( i i i ) HYPOTHETICAL: No ( i v ) ANTI-SENSE: No ( v i ) ORIGINAL SOURCE:
    ( B ) STRAIN:
    ( C ) INDIVIDUAL ISOLATE:
    ( D ) DEVELOPMENTAL STAGE:
    ( F ) TISSUE TYPE:
    ( G ) CELL TYPE:
    ( H ) CELL LINE:

( x i ) SEQUENCE DESCRIPTION: SEQ ID NO:5:

GTCGAGCCCG GGGAAATTAC TAAAACAATC ATC    33

( 2 ) INFORMATION FOR SEQ ID NO:6:

( i ) SEQUENCE CHARACTERISTICS:
    ( A ) LENGTH: 31
    ( B ) TYPE: nucleic acid
    ( C ) STRANDEDNESS: single
    ( D ) TOPOLOGY: linear ( i i ) MOLECULE TYPE:
    ( A ) DESCRIPTION: other nucleic acid ( i i i ) HYPOTHETICAL: No ( i v ) ANTI-SENSE: No ( v i ) ORIGINAL SOURCE:
    ( B ) STRAIN:
    ( C ) INDIVIDUAL ISOLATE:
    ( D ) DEVELOPMENTAL STAGE:
    ( F ) TISSUE TYPE:
    ( G ) CELL TYPE:
    ( H ) CELL LINE:

( x i ) SEQUENCE DESCRIPTION: SEQ ID NO:6:

GAGTTTGCGA CCAACATTAT CGCTTAATGT G    31

( 2 ) INFORMATION FOR SEQ ID NO:7:

( i ) SEQUENCE CHARACTERISTICS:
    ( A ) LENGTH: 31
    ( B ) TYPE: nucleic acid
    ( C ) STRANDEDNESS: single
    ( D ) TOPOLOGY: linear (i i) MOLECULE TYPE:
    (A) DESCRIPTION: other nucleic acid (i i i) HYPOTHETICAL: No (i v) ANTI-SENSE: No (v i) ORIGINAL SOURCE:
    (B) STRAIN:
    (C) INDIVIDUAL ISOLATE:
    (D) DEVELOPMENTAL STAGE:
    (F) TISSUE TYPE:
    (G) CELL TYPE:
    (H) CELL LINE:

(x i) SEQUENCE DESCRIPTION: SEQ ID NO:7:

ATGTTGGTCG ACAAACTCAT GGTATCTCAA C      31

(2) INFORMATION FOR SEQ ID NO:8:

(i) SEQUENCE CHARACTERISTICS:
    (A) LENGTH: 30
    (B) TYPE: nucleic acid
    (C) STRANDEDNESS: single
    (D) TOPOLOGY: linear (i i) MOLECULE TYPE:
    (A) DESCRIPTION: other nucleic acid (i i i) HYPOTHETICAL: No (i v) ANTI-SENSE: No (v i) ORIGINAL SOURCE:
    (B) STRAIN:
    (C) INDIVIDUAL ISOLATE:
    (D) DEVELOPMENTAL STAGE:
    (F) TISSUE TYPE:
    (G) CELL TYPE:
    (H) CELL LINE:

(x i) SEQUENCE DESCRIPTION: SEQ ID NO:8:

GAACGCGCAT GCCTTCATAG TGTCATTGAG      30

(2) INFORMATION FOR SEQ ID NO:9:

(i) SEQUENCE CHARACTERISTICS:
    (A) LENGTH: 24
    (B) TYPE: nucleic acid
    (C) STRANDEDNESS: single
    (D) TOPOLOGY: linear (i i) MOLECULE TYPE:
    (A) DESCRIPTION: other nucleic acid (i i i) HYPOTHETICAL: No (i v) ANTI-SENSE: No (v i) ORIGINAL SOURCE:
    (B) STRAIN:
    (C) INDIVIDUAL ISOLATE:
    (D) DEVELOPMENTAL STAGE:
    (F) TISSUE TYPE:
    (G) CELL TYPE:
    (H) CELL LINE:

(x i) SEQUENCE DESCRIPTION: SEQ ID NO:9:

ACAGCTTCCG GTTAATAGG TGTA      24

(2) INFORMATION FOR SEQ ID NO:10:

(i) SEQUENCE CHARACTERISTICS:
    (A) LENGTH: 18

```
            ( B ) TYPE: nucleic acid
            ( C ) STRANDEDNESS: single
            ( D ) TOPOLOGY: linear ( i i ) MOLECULE TYPE:
            ( A ) DESCRIPTION: other nucleic acid ( i i i ) HYPOTHETICAL: No ( i v ) ANTI-SENSE: No ( v i ) ORIGINAL SOURCE:
            ( B ) STRAIN:
            ( C ) INDIVIDUAL ISOLATE:
            ( D ) DEVELOPMENTAL STAGE:
            ( F ) TISSUE TYPE:
            ( G ) CELL TYPE:
            ( H ) CELL LINE:

( x i ) SEQUENCE DESCRIPTION: SEQ ID NO:10:

CATAAAAACC CCTCCTTA                                                             18

( 2 ) INFORMATION FOR SEQ ID NO:11:

( i ) SEQUENCE CHARACTERISTICS:
            ( A ) LENGTH: 23
            ( B ) TYPE: nucleic acid
            ( C ) STRANDEDNESS: double
            ( D ) TOPOLOGY: linear ( i i ) MOLECULE TYPE:
            ( A ) DESCRIPTION: other nucleic acid ( i i i ) HYPOTHETICAL: No ( i v ) ANTI-SENSE: No ( v i ) ORIGINAL SOURCE:
            ( B ) STRAIN:
            ( C ) INDIVIDUAL ISOLATE:
            ( D ) DEVELOPMENTAL STAGE:
            ( F ) TISSUE TYPE:
            ( G ) CELL TYPE:
            ( H ) CELL LINE:

( x i ) SEQUENCE DESCRIPTION: SEQ ID NO:11:

ATGCACTTGT ATTCGTTATA CTG                                                       23

( 2 ) INFORMATION FOR SEQ ID NO:12:

( i ) SEQUENCE CHARACTERISTICS:
            ( A ) LENGTH: 24
            ( B ) TYPE: nucleic acid
            ( C ) STRANDEDNESS: single
            ( D ) TOPOLOGY: linear ( i i ) MOLECULE TYPE:
            ( A ) DESCRIPTION: other nucleic acid ( i i i ) HYPOTHETICAL: No ( i v ) ANTI-SENSE: No ( v i ) ORIGINAL SOURCE:
            ( B ) STRAIN:
            ( C ) INDIVIDUAL ISOLATE:
            ( D ) DEVELOPMENTAL STAGE:
            ( F ) TISSUE TYPE:
            ( G ) CELL TYPE:
            ( H ) CELL LINE:

( x i ) SEQUENCE DESCRIPTION: SEQ ID NO:12:

AGGCCACTCT TAGTCTGCTT ACAT                                                      24
```

( 2 ) INFORMATION FOR SEQ ID NO:13:

( i ) SEQUENCE CHARACTERISTICS:
    ( A ) LENGTH: 17
    ( B ) TYPE: nucleic acid
    ( C ) STRANDEDNESS: single
    ( D ) TOPOLOGY: linear ( i i ) MOLECULE TYPE:
    ( A ) DESCRIPTION: other nucleic acid ( i i i ) HYPOTHETICAL: No ( i v ) ANTI-SENSE: No ( v i ) ORIGINAL SOURCE:
    ( B ) STRAIN:
    ( C ) INDIVIDUAL ISOLATE:
    ( D ) DEVELOPMENTAL STAGE:
    ( F ) TISSUE TYPE:
    ( G ) CELL TYPE:
    ( H ) CELL LINE:

( x i ) SEQUENCE DESCRIPTION: SEQ ID NO:13:

AGTGGTTACT AATACTG                                   17

( 2 ) INFORMATION FOR SEQ ID NO:14:

( i ) SEQUENCE CHARACTERISTICS:
    ( A ) LENGTH: 17
    ( B ) TYPE: nucleic acid
    ( C ) STRANDEDNESS: single
    ( D ) TOPOLOGY: linear ( i i ) MOLECULE TYPE:
    ( A ) DESCRIPTION: other nucleic acid ( i i i ) HYPOTHETICAL: No ( i v ) ANTI-SENSE: No ( v i ) ORIGINAL SOURCE:
    ( B ) STRAIN:
    ( C ) INDIVIDUAL ISOLATE:
    ( D ) DEVELOPMENTAL STAGE:
    ( F ) TISSUE TYPE:
    ( G ) CELL TYPE:
    ( H ) CELL LINE:

( x i ) SEQUENCE DESCRIPTION: SEQ ID NO:14:

CAGGATAGAT TGGTTTA                                   17

( 2 ) INFORMATION FOR SEQ ID NO:15:

( i ) SEQUENCE CHARACTERISTICS:
    ( A ) LENGTH: 22
    ( B ) TYPE: nucleic acid
    ( C ) STRANDEDNESS: single
    ( D ) TOPOLOGY: linear ( i i ) MOLECULE TYPE:
    ( A ) DESCRIPTION: other nucleic acid ( i i i ) HYPOTHETICAL: No ( i v ) ANTI-SENSE: No ( v i ) ORIGINAL SOURCE:
    ( B ) STRAIN:
    ( C ) INDIVIDUAL ISOLATE:
    ( D ) DEVELOPMENTAL STAGE:
    ( F ) TISSUE TYPE:
    ( G ) CELL TYPE:
    ( H ) CELL LINE:

( x i ) SEQUENCE DESCRIPTION: SEQ ID NO:15:

TATGTAAGCA GACTAAGAGT GG 22

(2) INFORMATION FOR SEQ ID NO:16:

(i) SEQUENCE CHARACTERISTICS:
        (A) LENGTH: 22
        (B) TYPE: nucleic acid
        (C) STRANDEDNESS: single
        (D) TOPOLOGY: linear (ii) MOLECULE TYPE:
        (A) DESCRIPTION: other nucleic acid (iii) HYPOTHETICAL: No (iv) ANTI-SENSE: No (vi) ORIGINAL SOURCE:
        (B) STRAIN:
        (C) INDIVIDUAL ISOLATE:
        (D) DEVELOPMENTAL STAGE:
        (F) TISSUE TYPE:
        (G) CELL TYPE:
        (H) CELL LINE:

(xi) SEQUENCE DESCRIPTION: SEQ ID NO:16:

TATGTTTTAT TTATGGGGA GG 22

(2) INFORMATION FOR SEQ ID NO:17:

(i) SEQUENCE CHARACTERISTICS:
        (A) LENGTH: 21
        (B) TYPE: nucleic acid
        (C) STRANDEDNESS: single
        (D) TOPOLOGY: linear (ii) MOLECULE TYPE:
        (A) DESCRIPTION: other nucleic acid (iii) HYPOTHETICAL: No (iv) ANTI-SENSE: No (vi) ORIGINAL SOURCE:
        (B) STRAIN:
        (C) INDIVIDUAL ISOLATE:
        (D) DEVELOPMENTAL STAGE:
        (F) TISSUE TYPE:
        (G) CELL TYPE:
        (H) CELL LINE:

(xi) SEQUENCE DESCRIPTION: SEQ ID NO:17:

TTTAAGGAAT GTATTTGTT A 21

(2) INFORMATION FOR SEQ ID NO:18:

(i) SEQUENCE CHARACTERISTICS:
        (A) LENGTH: 24
        (B) TYPE: nucleic acid
        (C) STRANDEDNESS: single
        (D) TOPOLOGY: linear (ii) MOLECULE TYPE:
        (A) DESCRIPTION: other nucleic acid (iii) HYPOTHETICAL: No (iv) ANTI-SENSE: No (vi) ORIGINAL SOURCE:
        (B) STRAIN:
        (C) INDIVIDUAL ISOLATE:
        (D) DEVELOPMENTAL STAGE:
        (F) TISSUE TYPE:

( G ) CELL TYPE:
( H ) CELL LINE:

( x i ) SEQUENCE DESCRIPTION: SEQ ID NO:18:

ATGCACATTT TAGTAACAGG GTTC 24

( 2 ) INFORMATION FOR SEQ ID NO:19:

( i ) SEQUENCE CHARACTERISTICS:
( A ) LENGTH: 22
( B ) TYPE: nucleic acid
( C ) STRANDEDNESS: single
( D ) TOPOLOGY: linear ( i i ) MOLECULE TYPE:
( A ) DESCRIPTION: other nucleic acid ( i i i ) HYPOTHETICAL: No ( i v ) ANTI-SENSE: No ( v i ) ORIGINAL SOURCE:
( B ) STRAIN:
( C ) INDIVIDUAL ISOLATE:
( D ) DEVELOPMENTAL STAGE:
( F ) TISSUE TYPE:
( G ) CELL TYPE:
( H ) CELL LINE:

( x i ) SEQUENCE DESCRIPTION: SEQ ID NO:19:

CGATTACGCT CATGTTTAGC AC 22

( 2 ) INFORMATION FOR SEQ ID NO:20:

( i ) SEQUENCE CHARACTERISTICS:
( A ) LENGTH: 22
( B ) TYPE: nucleic acid
( C ) STRANDEDNESS: single
( D ) TOPOLOGY: linear ( i i ) MOLECULE TYPE:
( A ) DESCRIPTION: other nucleic acid ( i i i ) HYPOTHETICAL: No ( i v ) ANTI-SENSE: No ( v i ) ORIGINAL SOURCE:
( B ) STRAIN:
( C ) INDIVIDUAL ISOLATE:
( D ) DEVELOPMENTAL STAGE:
( F ) TISSUE TYPE:
( G ) CELL TYPE:
( H ) CELL LINE:

( x i ) SEQUENCE DESCRIPTION: SEQ ID NO:20:

TCGATCCAAG ACATACAACT GG 22

USE OF CNA, FNBA, FNBB, AND HLB, GENE PROBES FOR THE STRAIN-SPECIFIC IDENTIFICATION OF *STAPHYLOCOCCUS AUREUS*

BACKGROUND OF THE INVENTION

1. Field of the Invention

The present invention relates generally to the fields of immunology and protein chemistry. More specifically, the present invention relates to the use of cna, fnbA, fnbB and hlb gene probes for the strain-specific identification of *Staphylococcus aureus*.

2. Description of the Related Art

*Staphylococcus aureus* is among the most prominent pathogens in both community-acquired and nosocomial infections (17, 24). With regard to the latter, the close interaction between colonized patients and staff together with the increased susceptibility of the resident population often leads to nosocomial outbreaks associated with a single strain (12). Moreover, given the prevalence of antibiotics within the hospital, such outbreaks often involve *Staphylococcus aureus* strains that are resistant to a wide variety of antibiotics including methicillin (12).

The tendency of specific strains of *Staphylococcus aureus* to spread within a hospital has led to the evaluation of a number of techniques aimed at the strain-specific typing of clinical isolates. Included among these techniques are bacteriophage typing (11, 22, 23), biotyping (21, 23), multilocus enzyme electrophoresis (21), antimicrobial susceptibility testing (8, 9, 21, 23), plasmid profile analysis (9, 21, 22), site specific (6, 11, 16, 21, 23) and arbitrarily primed polymerase chain reaction evaluation (23), ribotyping (7, 21), insertion sequence typing (21), DNA fingerprinting based on both standard restriction fragment length polymorphisms (8, 11, 22, 23) and pulse-field analysis of large DNA fragments (3, 9, 11, 21, 23). Twelve independent typing techniques were recently compared by Tenover et al. (21). This comparison suggested that DNA-based typing techniques and immunoblotting were most appropriate for epidemiological studies. However, no single technique is capable of clearly grouping epidemiologically related strains to the exclusion of unrelated strains (21).

During the course of studies aimed at characterization of the binding capacity of clinical isolates of *Staphylococcus aureus* for different host matrix proteins and analysis of the genes encoding the adhesin responsible for this binding capacity, it was discovered that the genes encoding the collagen adhesin (cna) and fibronectin-binding proteins (fnbA and fnbB) exhibit a great deal of organizational diversity. Additionally, many strains of *Staphylococcus aureus* are lysogenized with one of a group of bacteriophages that are known to insert within the gene encoding β-toxin (hlb) (19).

The prior art is deficient in the lack of effective genotypic markers for the differentiation of clinical isolates of *Staphylococcus aureus*. The present invention fulfills this long-standing need and desire in the art.

SUMMARY OF THE INVENTION

The cna, fnbA, fnbB and hlb genes of *Staphylococcus aureus* encode a collagen adhesin (cna), fibronectin-binding proteins (fnbA and fnbB) and a β-toxin (hlb). Oligonucleotide primers were used in a PCR amplification of genomic DNA from various strains of *S. aureus* and DNA probes for these genes were generated. Each of the DNA probes hybridized with highly variable DNA fragments obtained by restriction enzyme digestion of *S. aureus* genomic DNA. This variability revolved around six characteristics: (1) the presence and absence of cna; (2) the number of repeats of a 561 base pair region of cna called the B domain; (3) HaeIII and HincII restriction site polymorphisms within and near the cna gene; (4) HaeIII-defined restriction site polymorphisms within the fnbA and fnbB genes; (5) the presence or absence of a lysogenic phage within the hlb structural gene; and (6) the size of the HindIII-defined fragments containing the phage/hlb junction fragments.

The present invention demonstrates that the cna, fnbA, fnbB and hlb genes are appropriate genotypic markers for the differentiation of clinical isolates of *Staphylococcus aureus*. This differentiation was demonstrated during the course of an outbreak of methicillin-resistant *Staphylococcus aureus* in the neonatal intensive care units of two hospitals. The results demonstrate that genomic fingerprinting based on the hybridization profiles observed in Southern blots utilizing DNA probes for cna, fnbA, fnbB and hlb offer a viable alternative for the identification of clinical isolates of *Staphylococcus aureus*.

Genomic fingerprinting was employed to investigate a concomitant outbreak of methicillin-resistant *Staphylococcus aureus* (MRSA) in the neonatal intensive care unit (NICU) of two hospitals. The hospitals are located in the same city and are part of the same medical care system. Fingerprinting was done by Southern blot hybridization using DNA probes for the genes encoding the *Staphylococcus aureus* collagen adhesin (cna), fibronectin-binding proteins (fnbA, fnbB) and β-toxin (hlb). Genomic DNA was digested with HaeIII (cna and fnbA/fnbB probes) or HindIII (hlb probe). Hybridization patterns could be distinguished based on 1) the presence or absence of cna, 2) the size of the cna gene, 3) organization of the fnbA and fnbB genes, 4) the presence of a lysogenic phage within hlb and 5) the size of the restriction fragments containing the phage/bacterial DNA junction fragments.

Over a period of 4 months, a total of 46 isolates which were obtained from various wards within each hospital were examined. Among these 46 isolates, a total of 4 cna patterns was observed, 11 fnbA/fnbB patterns and 11 hlb patterns. Southern blots using HaeIII-digested genomic DNA and a combination of all 3 gene probes revealed a total of 16 clearly distinguishable patterns. 22 of the 46 isolates were identical with respect to every genomic marker examined. 21 of these 22 isolates were obtained from patients within an neonatal intensive care unit. 19 of 21 isolates also exhibited an identical antibiotic-resistance profile (antibiogram). Although 5 of the remaining 24 strains exhibited an antibiogram identical to the neonatal intensive care unit isolates, all 24 strains could be distinguished from the neonatal intensive care unit isolates by at least one genomic marker. These results suggest that the neonatal intensive care unit isolates had a common origin.

The present invention demonstrates that genomic fingerprinting using the cna, fnbA, fnbB and hlb gene probes can provide an important epidemiological tool for the identification of clinical isolates of *Staphylococcus aureus*.

In one embodiment of the present invention, there is provided a method of clinically differentiating the presence of *Staphylococcus aureus* in isolated samples, comprising the step of:

analyzing the hybridization profile observed in Southern blots utilizing DNA probes for genes selected from the group consisting of the cna gene, the fnbA gene, the fnbB gene, the hlb gene, the cna-up gene, the pcp gene, the pcp12 gene and the pcp34 gene.

In another embodiment of the present invention, there is provided a kit for clinically differentiating the presence of *Staphylococcus aureus* in isolated samples, comprising: (1) restriction enzymes to digest genomic DNA contained in said samples; and (2) DNA probes for genes selected from the group consisting of the cna gene, the fnbA gene, the fnbB gene, the hlb gene, the cna-up gene, the pcp gene, the pcp12 gene and the pcp34 gene.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
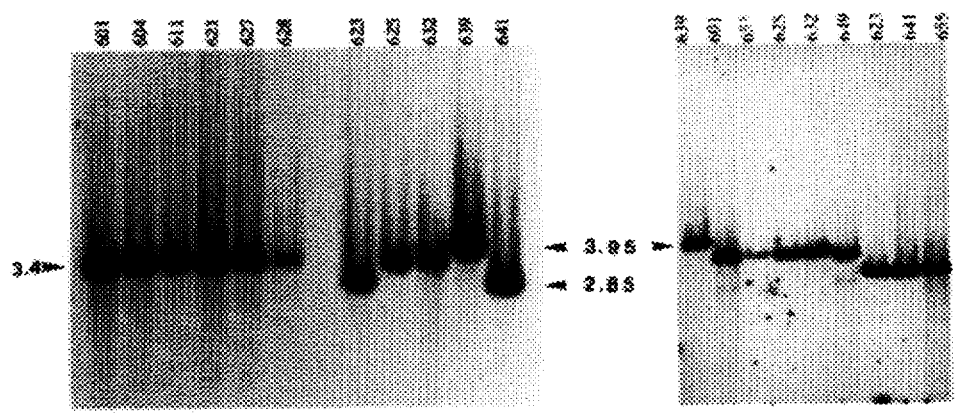
FIG. 1 shows the hybridization patterns obtained with the cna gene probe. Genomic DNA isolated from the indicated strains (top) was digested with HaeIII and hybridized with a 2.5 kbp DNA fragment containing the entire cna gene cloned from UAMS-1. The 6 strains shown on the far left are representative of the 21 neonatal intensive care unit isolates. With the exception of 639, the strains shown in the middle panel were isolated from units other than the neonatal intensive care unit. The panel on the right, which includes strains from the second outbreak, was run to confirm the size of each hybridizing fragment. Approximate sizes are indicated in kbp.

The present invention is directed to a method of clinically differentiating the presence of *Staphylococcus aureus* in isolated samples, comprising the step of: analyzing the hybridization profile observed in Southern blots utilizing DNA probes for genes selected from the group consisting of the cna gene, the fnbA gene, the fnbB gene, the hlb gene, the cna-up gene, the pcp gene, the pcp12 gene and the pcp34 gene.

In one embodiment, the genomic DNA contained in said samples is digested with an enzyme selected from the group consisting of HaeIII and HindIII. Preferably, the genomic DNA contained in said samples is digested with both HaeIII and HindIII.

In general, the hybridization profiles are distinguished based on factors selected from the group consisting of the presence or absence of cna, the size of the cna gene, organization of the fnbA and fnbB genes, the presence of a lysogenic phage within hlb and the size of the restriction fragments containing the phage/bacterial DNA junction fragments.

In the method of the present invention, probes to the cna-up gene can be used to differentiate between isolates that are cna-positive and isolates that are cna-negative. Similarly, a pcp12 gene probe can be used to detects HaeIII restriction site polymorphisms between cna and pcp. Thus, the pcp12 gene probe can be used to differentiate between isolates that are cna-positive and isolates that are cna-negative.

The present invention is also directed to a kit for clinically differentiating the presence of *Staphylococcus aureus* in isolated samples, comprising: (1) restriction enzymes to digest genomic DNA contained in said samples; (2) DNA probes for genes selected from the group consisting of the cna gene, the fnbA gene, the fnbB gene, the hlb gene, the cna-up gene, the pcp gene, the pcp12 gene and the pcp34 gene. In another embodiment, the kit further comprising a means for analyzing the hybridization profile observed in Southern blots. Preferably, the restriction enzymes are selected from the group consisting of HaeIII and HindIII.

The following examples are given for the purpose of illustrating various embodiments of the invention and are not meant to limit the present invention in any fashion.

EXAMPLE 1

Bacterial strains

Clinical isolates of Staphylococcus aureus were obtained from various wards within each of two hospitals (Table 1), both of which are located in the same city and are part of the same medical care system. The hospitals are distinguished herein as H1 or H2 (Table 1). Each isolate was plated on sheep blood agar and its identity confirmed by microscopic analysis and by demonstrating the production of both catalase and congulase (24). Antibiotic-sensitivity profiles (antibiograms) were determined with the Vitek system (bioMerieux Vitek, Inc., Hazelwood, Mo.) using cephalothin (Cph), ciprofloxacin (Cip), clindamycin (Cln), erythromycin (Erm), oxacillin (Ox), penicillin-G (Pen), trimethoprim/ sulfoxamide (TS), tetracycline and vancomycin (Van). The minimum inhibitory concentrations interpreted as conferring resistance were: Cph, $\geq 32$ µg/ml; Cip, $\geq 4$ µg/ml; Cln, $\geq 8$ µg/ml; Erm, $\geq 8$ µg/ml; Ox, $\geq 8$ µg/ml; Pen, $\geq 16$ µg/ml; TS, $\geq 150$ µg/ml and Tet, $\geq 16$ µg/ml.

TABLE I

| | Bacterial strains | | | |
|---|---|---|---|---|
| | | Isolated from: | | |
| Iso-late[1] | Site | Ward[2] | (Hospital[3]) | Antibiogram[4] |
| 601 | Wound | NICU | (H1) | Cph*, Cip*, Cln*, Erm*, Ox*, Pen*, TS*, Tet*, Van* |
| 602 | Wound | NICU | (H1) | 601*5 |
| 603 | Wound | NeICU | (H1) | Cip*, TS* |
| 604 | Blood | NICU | (H1) | 601 |
| 605 | Blood | 4C | (H1) | TS* |
| 609 | Blood | 2A | (H1) | Cph*, Cip*, Cln*, Ox*, TS* |
| 610 | Blood | NICU | (H1) | 601 |
| 611 | Tracheal culture | NICU | (H2) | 601 |
| 612 | Chest tube | NICU | (H1) | 601 |
| 613 | Hip aspirate | NICU | (H2) | 601 |
| 614 | Tracheal culture | NICU | (H2) | Cph*, Cln*, TS* |
| 615 | Tracheal culture | NICU | (H2) | 601 |
| 616 | Blood | NICU | (H1) | 601 |
| 620 | Wound | 4C | (H1) | TS* |
| 621 | Wound | NICU | (H2) | 601 |
| 622 | Pleural fluid | 2B | (H1) | Cph*, Cip*, Cln*, Erm*, Ox*, TS* Tet* |
| 623 | Wound | 4B | (H1) | Cph*, Cip*, Cin*, Erm*, Ox*, Pen*, TS* |
| 624 | Wound | DC | (H1) | Cph*, Cip*, Cln*, Ox*, TS* |
| 625 | Abscess | 2A | (H1) | Cph*, Cip*, Cln*, Ox*, TS* |

TABLE I-continued

| | Bacterial strains | | | |
|---|---|---|---|---|
| | | Isolated from: | | |
| Iso-late[1] | Site | Ward[2] | (Hospital[3]) | Antibiogram[4] |
| 626 | Nasal swab | NICU | (H1) | 601 |
| 627 | Wound | NICU | (H1) | 601 |
| 628 | Nasal swab | NICU | (H1) | 601 |
| 630 | Nasal swab | NICU | (H1) | 601 |
| 631 | Nasal swab | NICU | (H1) | 601 |
| 632 | Wound | ODS | (H1) | Cph*, Cip*, Cln*, Erm*, Ox*, TS* |
| 633 | BAL[6] | SICU | (H1) | 601 |
| 634 | Blood | 2B | (H1) | 601 |
| 635 | Blood | 4B | (H1) | Cph*, Cip*, Cln*, Erm*, Ox*, TS* |
| 636 | Wound | OC | (H1) | Cph*, Cip*, Cln*, Erm*, Ox*, TS* |
| 637 | Nasal swab | NICU | (H1) | 601 |
| 638 | BAL | SICU | (H1) | 601 |
| 639 | Tracheal culture | NICU | (H1) | 601 |
| 640 | Abscess | DC | (H1) | Cph*, Cip*, Cln*, Erm*, Ox*, TS* |
| 641 | Blood | 7A | (H1) | Tets, TSs |
| 642 | Blood | 3B | (H1) | Cph*, Cip*, Cln*, Ox*, TS* |
| 645 | Blood | 3A | (H1) | Not determined |
| 646 | Tracheal culture | NICU | (H1) | 601 |
| 647 | Catheter | NICU | (H1) | 601 |
| 648 | Tracheal culture | NICU | (H2) | TS* |
| 649 | Blood | SICU | (H1) | 601 |
| 652 | Blood | 4B | (H1) | Cph*, Cip*, Cln*, Erm*, Ox*, TS* |
| 653 | Sputum | NICU | (H1) | 601 |
| 654 | Wound | 2A | (H1) | Cph*, Cip*, Cln*, Erm*, Ox*, Pen*, TS* |
| 655 | Blood | 3C | (H1) | Not determined |
| 656 | Eye | NICU | (H1) | 601 |
| 657 | Joint | ER | (H1) | TS* |

For the results shown in TABLE I, the footnote 1 indicates all isolates submitted for genomic analysis were submitted out clinical information and assigned a number based only on order of submission. Footnote 2 indicates that ward designations de: NICU, neonatal intensive care unit; NEICU; neurology intensive unit; SICU, surgical intensive care unit; DC, dermatology clinic; ODS, one-day surgery; ER, emergency room; OC, oncology clinic. Other designations are for general medicine or surgery wards. Footnote 3 indicates that the two hospitals that submitted isolates are distinguished parenthetically as H1 and H2. Footnote 4 indicates that abbreviations used include: Cph, Cephalothim; Cip, ciprofloxacin; Cln, clindamycin; Erm, erythromycin; Ox, oxacillin; Pen, penicillin-G; TS, trimethoprim/ sulfa; Tet, tetracycline; Van, vancomycin. Footnote 5 indicates that 601 refers to the resistance pattern observed in UAMS-601. In those cases in which the antibiogram differed from that observed in UAMS-601, only those antibiotics for which the sensitivity pattern differed are shown. Footnote 6 indicates that BAL stands for broncho-alveolar lavage.

Each isolate submitted for genomic characterization was assigned a number based only on the order of submission. The clinical history of each isolate and its antibiogram were not revealed to the laboratory responsible for genomic characterization. Additional *Staphylococcus aureus* strains used for some experiments included S6C, UAMS-1, Phillips and Cowan I, all of which have been described elsewhere (4, 5, 14, 20).

EXAMPLE 2
Genomic fingerprinting

Genomic DNA was isolated from each strain as previously described (18). For Southern blots, genomic DNA was digested with HindIII or HaeIII and electrophoresed in 0.8% agarose. After transfer to nylon membranes, immobilized DNA was hybridized under stringent conditions (18) using DNA probes for the genes encoding the *Staphylococcus aureus* collagen adhesin (cna), fibronectin-binding proteins (fnbA and fnbB) and β-toxin (hlb). Probes for cna, fnbA and fnbB were generated by polymerase chain reaction amplification of genomic DNA from strains UAMS-1 (cna) or S6C (fnbA/fnbB). The cna gene was amplified using the oligonucleotide primers and amplification conditions described by Patti et al. (14). 5'ATGCACTTGTATTCGTTATACTG (SEQ ID NO: 1), 3'AGGCCACTCTTAGTCTGCTTACAT (SEQ ID NO: 2). These primers amplified a 2.5 kbp fragment containing the entire UAMS-1 cna gene (5). Amplification was done in the following steps: 1) 94C, 2 minutes; 2) 94C, 1 minute; 3) 55C, 1 minute; 4) 72C, 1 minute; steps 2–4 repeated 30 times; 5) 72C, 5 minutes.

Primers used for amplification of the fnbA and fnbB genes are shown in TABLE II. These primers amplify contiguous fragments that collectively span the entire 6.8 kbp region encoding fnbA and fnbB (2, 10). In all cases, comments related to hybridization with the fnbA and fnbB gene probe refer to the simultaneous use of all 3 of the amplification products described in TABLE II. The hlb gene probe consisted of a 2.6 kbp HindIII fragment containing the entire hlb gene cloned from *Staphylococcus aureus* strain M60 (19). Importantly, this clone includes a 0.4 kbp fragment that is located immediately upstream of the 5' end of hlb (19) and is not present in other functional hlb clones (15). DNA fragments used as probes were labelled with digoxygenin 11-dUTP as previously described (18).

EXAMPLE 3
Hybridization patterns observed with the cna gene probe

A primary distinguishing characteristic with respect to the *Staphylococcus aureus* collagen adhesin gene (cna) was its presence or absence among different clinical isolates. Specifically, when genomic DNA was digested with HaeIII and probed with a 2.5 kbp DNA fragment containing the entire cna gene, a single hybridizing fragment was observed in 28 of 46 strains (FIG. 1). The presence of a single HaeIII fragment that hybridizes with cna is consistent with the published sequence of the *Staphylococcus aureus* cna gene (14). While these results suggest that most strains encode cna, it is believed that at least 21 of the 28 cna+ strains are epidemiologically related (see below). This observation suggests that most strains do not encode cna and that its presence may be a relatively discriminating characteristic of individual *Staphylococcus aureus* strains. Moreover, strains that encoded cna could be distinguished from each other by the size of the HaeIII fragment that hybridized with the cna probe. Specifically, hybridizing fragments of 3.95, 3.4 and 2.85 kbp were observed (FIG. 1).

To date, 3 forms of the cna gene have been described (5, 13). These forms differ in the number of repeats (1, 2 or 3) of a 561 base pair region designated the B domain (5, 13). The *Staphylococcus aureus* cna gene listed in the GenBank database (accession #M81736) represents the form of cna that includes 3 direct repeats of the B domain. The GenBank sequence also includes 2 HaeIII restriction sites located at nucleotide 231 of the cna structural gene and 105 nucleotides (nt) downstream from the cna stop codon. These sites, which correspond to nucleotides 381 and 3806 of the published DNA sequence that includes the cna gene (14), are located on either side of the region that contains the B domains (5, 14). The position of the HaeIII restriction sites suggests that the 2.85 and 3.4 kbp fragments correspond to

TABLE II

Oligonucleotide primers for amplification of fnbA and fnbB Primer[1]:

| 5' | 3' | Size (amplified region[2]) |
|---|---|---|
| atcttagagctcactttcattaactcgct<br>SEQ ID NO: 3 | aatttcctagggctcgactggtccttctgc<br>SEQ ID NO: 4 | 2220bp(1-2220) |
| gtcgagcccggggaaattactaaaacaatcatc<br>SEQ ID NO: 5 | gagtttgcgaccaacattatcgcttaatgtg<br>SEQ ID NO: 6 | 2324bp(2210-4534) |
| atgttggtcgacaaactcatggtatctcaac<br>SEQ ID NO: 7 | gaacgcgcatgccttcatagtgtcattgag<br>SEQ ID NO: 8 | 2277bp(4523-5800) |

Footnote 1: oligonucleotides primers were constructed such that consecutive amplification products overlap with the overlap containing matching recognition sites for A val (underlined) or SalI (double underline). Additional restriction sites for SacI and spH (bold italics) were incorporated into the two terminal fragments to facilitate cloning into pUC vectors. All primers are listed 5' to 3'. 5' and 3' primers correspond to opposite strands of the template DNA.

Footnote 2: sequences are based on GenBank accession #J104151 (3342 base pairs) and #X62992 (3458 base pairs). These sequences correspond to fnbA and fnbB, respectively (2, 10). The two sequences were aligned end-to-end in the order J104151-X62992 to derive the entire 6800 base pair sequence. The alignment includes a 6 base pair (actagt) direct repeat spanning positions 3337 to 3348.

cna genes with two and three B domains respectively. Of the 28 strains that encoded cna, 24 appeared to encode a cna gene with three B domains while 3 appeared to encode a cna gene with two B domains (FIG. 1). None of the clinical isolates that were examined encoded a cna gene with a single B domain. 21 of the 24 isolates that encoded a cna gene with three B domains were neonatal intensive care unit isolates (TABLE I). Although only 19 of the 21 neonatal intensive care unit isolates exhibited the same antibiogram (TABLE I), all 21 strains also exhibited the same hybridization pattern with respect to both fnbA/fnbB and hlb (see below). One isolate (UAMS-649) matched the neonatal intensive care unit isolates in every respect except that it was not obtained from a neonatal intensive care unit patient (TABLE I). The 2 remaining strains that encoded a cna gene with three B domains (UAMS-625 and 632) was distinguished from the neonatal ICU isolates based on both antibiogram (TABLE I) and the hybridization pattern observed with other DNA probes (see below).

Figure 2:
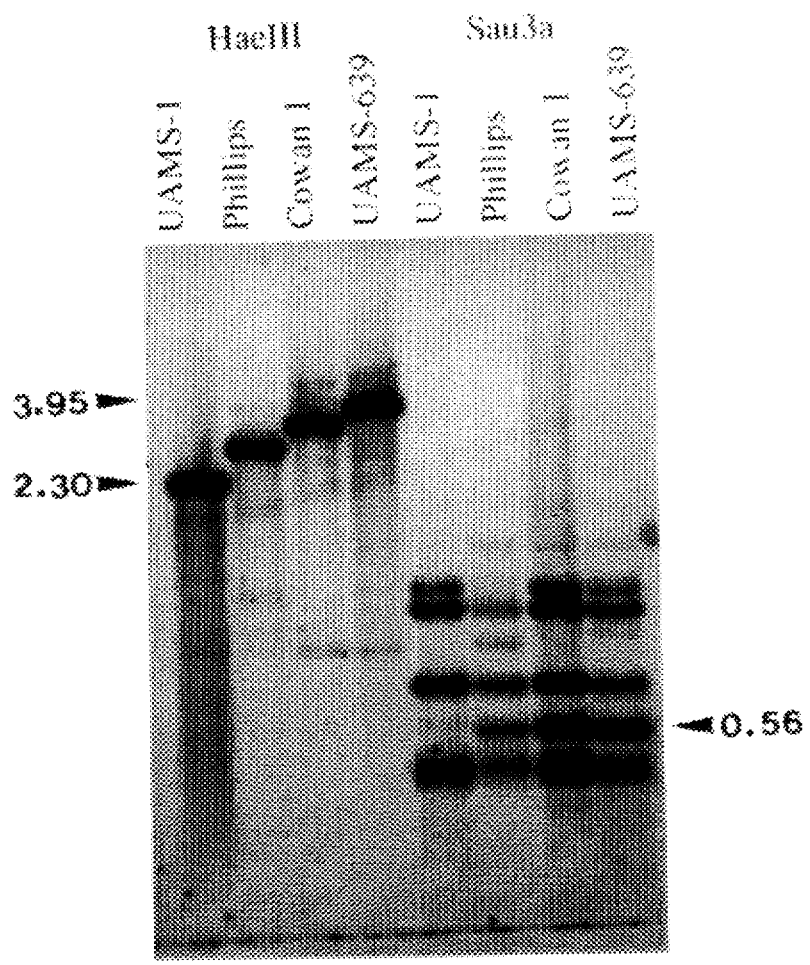
FIG. 2 shows the identity of the cna fragment in UAMS-639. Genomic DNA isolated from the indicated strains (top) was digested with HaeIII (left) or Sau3a (right) and probed with the 2.5 kbp cna fragment from UAMS-1. Approximate sizes are indicated in kbp.

When genomic DNA from UAMS-639 was digested with HaeIII and probed with cna, a single, 3.95 kbp fragment was observed (FIG. 1). The size of this fragment was unexpected based on the recognized forms of the cna gene (4, 13, 14). However, the fact that the 3.95 kbp fragment was approximately 550 base pairs larger than the corresponding fragment observed in strains thought to encode three B domains (FIG. 1) suggested that UAMS-639 might encode a previously unrecognized variant of cna that includes a fourth B domain. That was confirmed by hybridizing HaeIII and Sau3A-digested genomic DNA from UAMS-639 and from strains known to encode a cna gene with one, two or three B domains with a cna probe (FIG. 2). Specifically, when genomic DNA from UAMS-1, Phillips, Cowan I and UAMS-639 was digested with HaeIII and probed with cna, hybridizing fragments of 2.3, 2.85, 3.4 and 3.95 kbp were observed (FIG. 2). The 2.3, 2.85 and 3.4 kb fragments observed in UAMS-1, Phillips and Cowan I are consistent with the fact that these strains encode cna genes with one, two and three B domains respectively (5).

The observation that UAMS-639 encoded a HaeIII fragment that hybridized with cna and was approximately 550 base pairs larger than the corresponding fragment in strain Cowan I (FIG. 2) is consistent with the suggestion that UAMS-639 encodes a cna gene with four B domains. That was confirmed by hybridizing Sau3a-digested genomic DNA with the 2.5 kbp cna probe. Because the cna B domains are directly repeated and contain a single Sau3a restriction site (14), digestion with Sau3a would yield a 561 base pairs fragment in any strain that encodes more than one B domain (4). The presence of this 561 base pairs fragment, together with the conservation of all 4 of the flanking fragments observed in strains known to encode cna (FIG. 2) confirms the presence of a cna gene with four B domains in UAMS-639.

EXAMPLE 4

Hybridization patterns observed with the fnabA/fnbB gene probes

Figure 3:
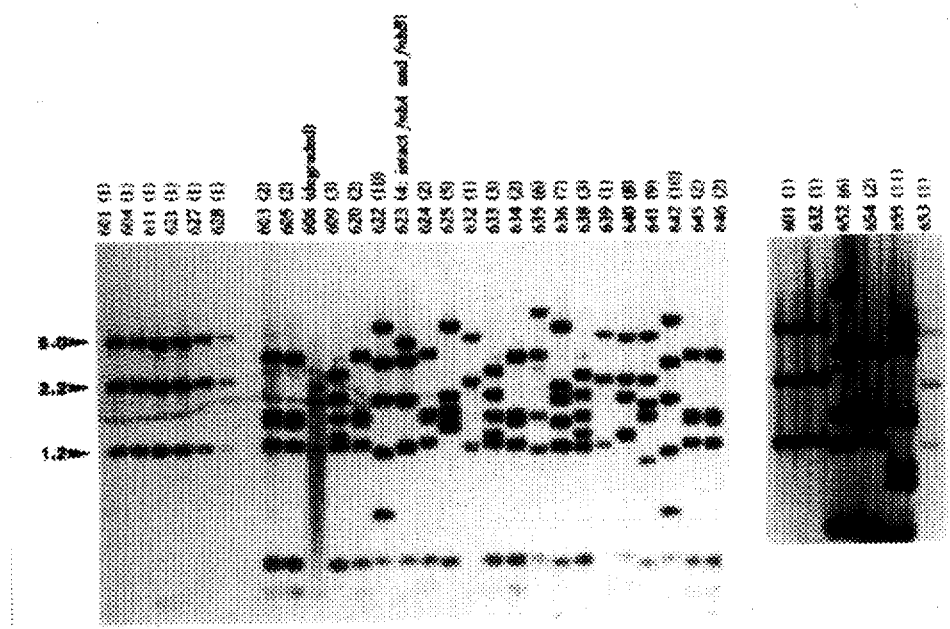
FIG. 3 shows the hybridization patterns obtained with the fnbA and fnbB gene probes. Genomic DNA isolated from the indicated strains (top) was digested with HaeIII and simultaneously hybridized with the 3 DNA fragments that span the fnbA and fnbB genes of strain S6C. Only 6 of the 21 identical neonatal intensive care unit isolates are shown (far left). Numbers in parenthesis designate distinct hybridization patterns. Because the DNA was too degraded to obtain a reliable analysis, UAMS-606 was excluded from further analysis. Based on the available sequence data, UAMS-623 (pattern #4) is thought to encode intact copies of both fnbA and fnbB. The panel on the far right is included because the pattern observed in UAMS-655 was unlike that observed in any other strain. Approximate sizes are indicated in kbp.

In contrast to the results obtained using a cna gene probe, all 46 clinical isolates encoded some form of the fibronectin-binding protein gene(s). At least some *Staphylococcus aureus* strains encode 2 fibronectin-binding protein genes designated fnbA (GenBank accession #J104151) and fnbB (GenBank accession #X62992) (2, 10). These two genes are very similar and, in at least some strains, are contiguous within the Staphylococcal chromosome (2, 10). Taken together, the region encoding fnbA and fnbB spans a total of approximately 6.8 kbp (2, 10). Based on the available sequence data, strains that encode both fibronectin-binding protein genes should exhibit 5 HaeIII restriction fragments that hybridize with DNA probes that span both fnbA and fnbB (2, 10). These 5 fragments include three (645, 1,214 and 1,993 base pairs) that are defined by internal HaeIII sites (2, 10). The only conclusion that can be drawn with respect to the size of the two terminal fragments is that one should be at least 897 base pairs and the other at least 2,351 base pairs (2, 10). Of the 46 strains that were examined, only one (UAMS-623) exhibited a hybridization pattern consistent with these predictions (FIG. 3). Specifically, UAMS-623 was found to have hybridizing fragments of approximately 5.0, 3.0, 2.0, 1.2 and 0.35 kbp (FIG. 3). Thus, UAMS-623 encodes intact copies of both fnbA and fnbB and that the 3.0 and 5.0 kbp HaeIII fragments represent terminal fragments that include some flanking DNA.

The remaining 45 strains that were examined exhibited a total of 10 different restriction patterns (FIG. 3). Five hybridization patterns were observed in only one strain while the remaining 5 patterns contained 2 (2 groups), 3, 9 and 24 strains (TABLE III). The group of 24 strains included the 21 strains from the neonatal intensive care unit. Of the 3 strains that matched the neonatal intensive care unit isolates, one (UAMS-649) could not be distinguished from the neonatal intensive care unit isolates by any parameter other than the fact that it was isolated from a different ward (TABLE I). A second isolate (UAMS-639) exhibited the same antibiogram but was distinguished from the neonatal intensive care unit isolates by the fact that it encoded a cna gene with four B domains (FIG. 1). The third strain (UAMS-632) encoded a cna gene identical to that observed in the neonatal intensive care unit isolates (FIG. 1) but could be distinguished from the neonatal intensive care unit isolates based on its hlb restriction profile (see below). Although, constructed of restriction maps of each of the distinct fnbA/fnbB profiles and correlation of each profile with the ability to bind fibronectin are in process, no attempt was made to define these profiles during the course to these epidemiological studies.

TABLE III

Summary of Southern blot patterns

|  | cna | fnbA/ fnbB | hlb | Combined probe |
|---|---|---|---|---|
| Total number of patterns | 4[1] | 11 | 11 | 16 |
| Number of strains matching isolates | 3 | 3 | 3 | 1 |
| Highest number of matching strains other than NICU isolates | 18[2] | 9 | 4[3] | 4[4] |
| Number of repeated hybridization patterns other than NICU isolates[5] | 3[6] | 5 | 7 | 6 |

Footnote 1: includes the group of strains that do not encode cna
Footnote 2: the 18 stains in this category were matched based on the fact that they did not encode cna.
Footnote 3: 4 groups of 4 strains exhibited the same or a very similar hlb restriction pattern.
Footnote 4: 2 groups of 4 strains exhibited the same or a very similar pattern.
Footnote 5: includes the pattern exhibited by the NICU isolates only if more than one additional strain exhibited the same hybridization pattern.
Footnote 6: includes the group of 18 strains that do not encode cna.

EXAMPLE 5

Hybridization patterns observed with the hlb gene probe

The results of the cna and fnbA/fnbB Southern blots defined a group of 23 strains, 21 of which were isolated from an neonatal intensive care unit (TABLE I). The other 2 strains (UAMS-632 and 649) were distinguished from the neonatal intensive care unit strains only by virtue of the fact that they were isolated from a different unit in the hospital and, in the case of UAMS-632, exhibited a different antibiogram (TABLE I). To further characterize these strains, the gene encoding *Staphylococcus aureus* β-toxin (hlb) was examined.

Figure 4:
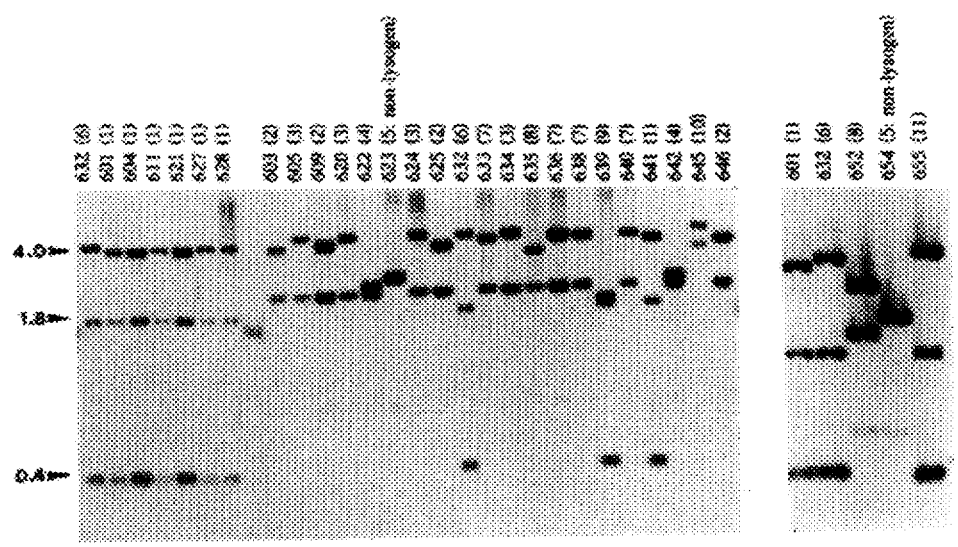
FIG. 4 shows the hybridization patterns obtained with the hlb gene probe. Genomic DNA from the indicated strains (top) was digested with HindIII and probed with a DNA fragment containing the entire hlb gene. Numbers in parenthesis designate individual hybridization patterns. UAMS-632 was run three times to confirm the size difference with respect to representative neonatal intensive care unit isolate (601, 604, 611, 621, 627 and 628). The panel on the right was included because the pattern observed in UAMS-655 was unlike that observed in any other strain. Approzimate sizes are indicated in kbp.

The choice of hlb was based on the fact that the att site of a group of at least 4 staphylococcal bacteriophages is known to reside within hlb (19). Of the 46 strains examined, only two (UAMS-623 and 654) were found to encode what appeared to be an intact hlb gene (FIG. 4). That conclusion is based on the observations that: 1) the hlb gene of *Staphylococcus aureus* has been cloned on a 2.2 kbp HindIII fragment that does not include any internal HindIII restriction sites (15); and 2) both UAMS-623 and 654 contained a single 2.2 kbp HindIII fragment that hybridized with the hlb probe (FIG. 4). The remaining 44 strains all exhibited at least two HindIII fragments that hybridized with the hlb probe (FIG. 4). These results suggest that these 44 strains are lysogenized with β-toxin converting bacteriophage (19).

A total of 10 hybridization patterns were observed among these 44 strains (FIG. 4). Other than the group that included the neonatal intensive care unit isolates, the largest group that exhibited the same hlb hybridization pattern contained 4 strains (TABLE III). A total of 26 isolates (including the 21 neonatal intensive care unit isolates) were found to encode a 0.4 kbp fragment that hybridized with the hlb probe (FIG. 4). This 0.4 kbp fragment can be explained by the presence of a HindIII restriction site polymorphism that occurs in the region immediately upstream from the hlb gene (19). Although the 0.4 kbp fragment was a distinguishing characteristic among the 46 strains examined, the fact that this polymorphism occurs in the region of the *Staphylococcus aureus* chromosome that flanks the hlb gene (19) demonstrates that the presence or absence of the 0.4 kbp fragment is not indicative of the lysogenic status of individual strains.

Of the 26 lysogenized strains that contained the 0.4 kbp hybridizing fragment, two (UAMS-632-639) were distinguished from the neonatal intensive care unit isolates by polymorphisms in 1 of the 2 DNA fragments containing the phage/hlb junctions (FIG. 4). The remaining 3 strains (UAMS-641, 649 and 657) exhibited the same hlb hybridization pattern as the 21 strains isolated from the neonatal intensive care unit (FIG. 4). However, UAMS-641 and 657 could be distinguished from the neonatal intensive care unit isolates in both the cna (FIG. 1) and fnbA/fnbB (FIG. 3) Southern blots. Only one strain (UAMS-649) could not be distinguished from the neonatal intensive care unit isolates on the basis of any of the genomic markers examined.

EXAMPLE 6
Hybridization patterns observed with a combination of all probes

Figure 5:
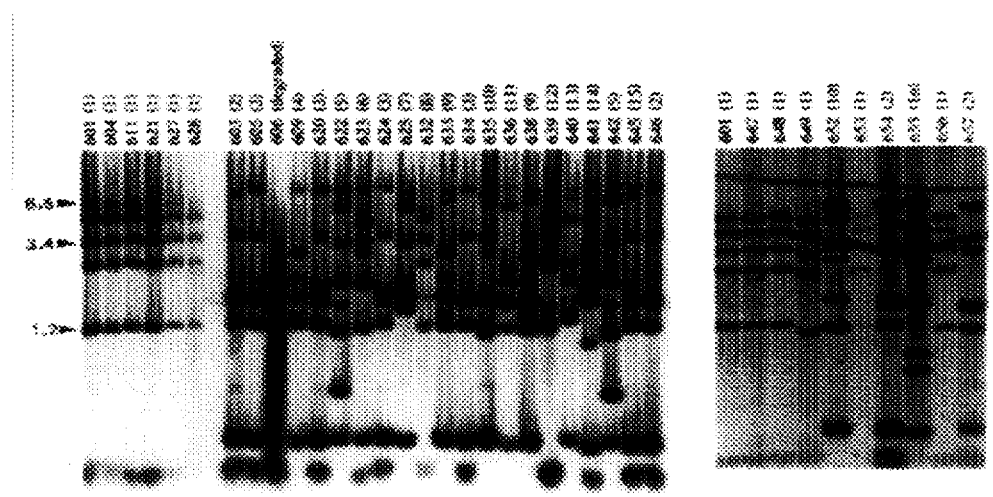
FIG. 5 shows the hybridization patterns obtained with the combined cna, fnbA/fnbB gene probes. Genomic DNA from the indicated strains (top) was digested with HaeIII and simultaneously probed with DNA fragments containing cna, fnbA, fnbB, hlb. UAMS-606 was not included in the analysis. Numbers in parenthesis designate individual hybridization patterns. The panel on the right shows the hybridization pattern obtained with each of the 9 isolates submitted during the course of the second outbreak. Approximate sizes are indicated in kbp.

In an effort to both confirm the results of the Southern blots using individual DNA probes and simplify the analysis by combing the overall results into a single Southern blot, HaeIII-digested genomic DNA was examined using a combination of the cna, fnbA, fnbB and hlb probes (FIG. 5). This analysis revealed a total of 16 restriction patterns (FIG. 5), 10 of which were observed in only 1 strain (TABLE III).

Other than the group that included the neonatal intensive care unit isolates, the largest group of strains that exhibited the same hybridization profile using the combined cna, fnbA/fnbB and hlb DNA probes contained a total of 4 strains (TABLE III). However, 8 strains (UAMS-603, 646, 654, 657, 605, 620, 624 and 634) were difficult to distinguish from each other when HaeIII-digested genomic DNA was probed simultaneously with the cna, fnbA/fnbB and hlb probes (FIG. 5). These difficulties appeared to be a function of the use of HaeIII (rather than HindIII). More specifically, because these 8 strains did not encode cna (FIG. 1) and exhibited the same hybridization profile with respect to fnbA and fnbB (FIG. 3), they could only be distinguished by their hlb hybridization profile (FIG. 4).

Figure 6:
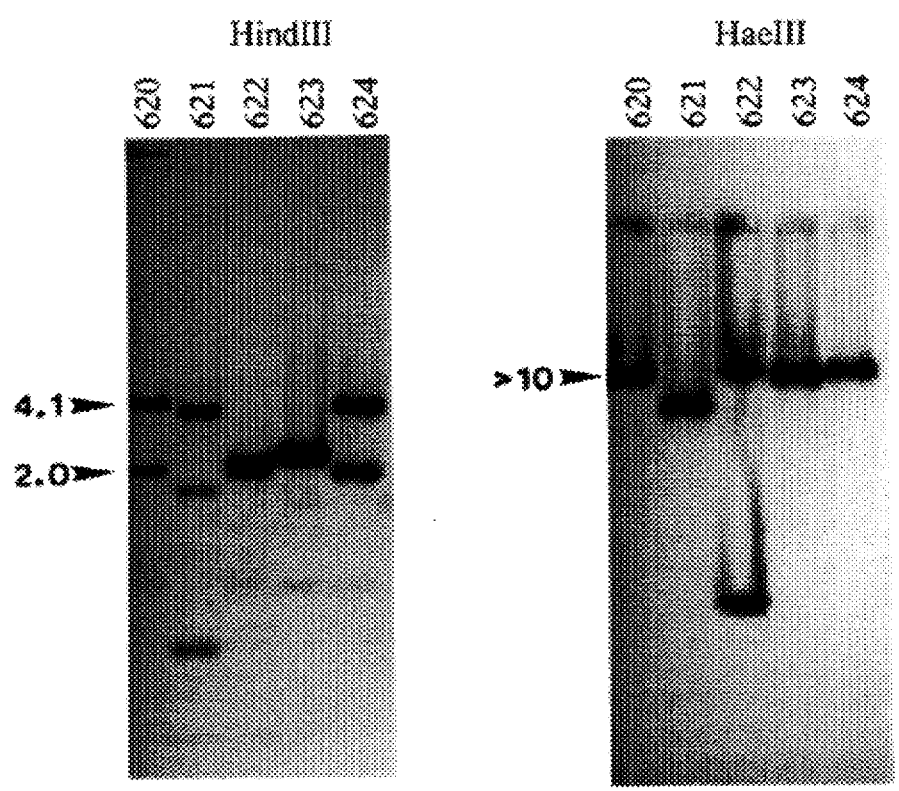
FIG. 6 shows the comparison of HaeIII and HindIII hlb blots. Genomic DNA isolated from selected strains (top) was digested with HindIII (left) or HaeIII (right) and probed with the hlb gene. Approximate sizes are indicated in kbp.

The hlb gene contains a single HaeIII site located approximately 155 base pairs downstream (3') from the recognized 14 base pairs phage att site (1, 15). The phage att site is located 170 base pairs from the 5' terminus of the hlb gene. Any lysogenized strain would therefore carry two HaeIII restriction fragments that collectively contain the terminal 325 base pairs of the 5' end of hlb (1, 15). These strains should therefore contain a total of 3 fragments (excluding the 0.4 kbp fragment discussed above) that hybridize with the hlb probe. However, 4 strains were examined that could be distinguished from each other on the basis of their HindIII/hlb hybridization profile and found that 3 of 4 exhibited a single HaeIII fragment that hybridized with the hlb (FIG. 6). These results suggest that 1) HaeIII digestion yields hlb fragments too small to efficiently hybridize with the hlb probe used in these experiments or 2) digestion with HaeIII yields genomic hlb fragments of similar size.

In any event, the use of HaeIII in hlb blots does not appear to be as discriminating as HindIII digests. For that reason, it was difficult to distinguish among the 8 strains on the basis of the HaeIII hybridization profiles (FIG. 5) despite the fact that the 8 strains could be divided into 2 groups of 4 on the basis of the hybridization pattern observed when HindIII-digested genomic DNA was probed with hlb (FIG. 4). However, it must be emphasized that the difficulties encountered in distinguishing among these 8 strains did not prevent the clear differentiation of all 8 strains from the neonatal intensive care unit isolates. In fact, all but one strain (UAMS-649) could be distinguished from the 21 neonatal intensive care unit isolates based on the results of the single Southern blot employing HaeIII-digested genomic DNA and gene probes for cna, fnbA, fnbB and hlb (FIG. 5). This strain was isolated from a different ward (Table 1). Moreover, it was isolated at least two months after the first isolation from the neonatal intensive care unit. The latter suggest that UAMS-649 may be epidemiologically related to the neonatal intensive care unit isolates and that its isolation from a ward other than the neonatal intensive care unit may be indicative of the spread of the neonatal intensive care unit strain within the hospital. It is also of interest to note that UAMS-649 was the last of 3 isolates obtained from the same patient and that the 2 isolates (UAMS-633 and 638) obtained prior to the isolation of UAMS-649 matched each other but did not match the neonatal intensive care unit isolates.

The epidemiological differentiation of clinical isolates of *Staphylococcus aureus* is an important consideration, particulary in the hospital where outbreaks associated with single strains are common (12). The importance of the ability to discriminate between *Staphylococcus aureus* isolates is evidenced by the number of techniques employed in that capacity. Tenover et al. (21) recently reported a comprehensive comparison of 12 typing techniques. Specific techniques included determination of antibiograms, bacteriophage typing, biotyping, restriction fragment length polymorphism (RFLP) analysis employing specific gene probes, insertion sequence (IS) probe typing, field-inversion gel electrophoresis (FIGE), immunoblotting, multilocus enzyme electrophoresis (MLEE), pulse-field gel electrophoresis (PFGE), polymerase chain reaction (PCR) analysis of the coagulase gene, restriction digest analysis of plasmid DNA and ribotyping (21). The analysis, which was carried out at 8 independent institutions, evaluated each technique with respect to typeability (the ability to provide an unambiguous result for each isolate), reproducibility (the ability to yield the same result in repeated tests), discriminatory power (the ability to distinguish between unrelated strains), ease of interpretation and ease of use (21). Although the latter are important considerations with respect to the widespread applicability of any typing technique, the importance of identifying the strain responsible for specific outbreaks dictate that they cannot overriding concerns that supersede considerations of typeability, reproducibility and discriminatory power. In the Tenover study (21), the total number of types observed among 60 well-characterized strains, 26 of which fell into one of 4 epidemiologically related groups, ranged from 7 (coagulase gene PCT) to 25 (PFGE and FIGE) (21). The number of strains correctly identified as belonging to one of the epedemiologically related groups ranged from 16 (IS typing) to 29 (ClaI-defined ribotyping) (21). The number of strains that were inappropriately classified ranged from 0 (plasmid profile analysis) to 8 (coagulase gene PCR) (21). In general, there was an inverse relationship between typeability and discriminatory power. For example, plasmid profile analysis revelaed a total 20 types and did not misidentify any strains but also failed to identify 6 epidemiologically-related strains (21). Similarly, ribotyping revealed a total of 9 types and correctly identified 29 of 29 epidemiologically-related strains but also resulted in the inclusion of 7 unrelated strains in the epidemiologically-related groups (21). A total of 46 isolates were examined during the course of an outbreak of methicillin-resistant *Staphylococcus aureus* in the neonatal intensive care units of two hospitals, both of which are part of the same medical care system. The outbreaks occurred during the same time period in each hospital. A total of 23 strains were submitted from colonized or infected patients in an neonatal intensive care unit. The remaining 23 strains were obtained from patients admitted to other wards within the same hospitals. Based on the analysis of the resistance patterns to 9 antibiotics, a total of 9 antibiograms were observed among the 46 strains.

With regard to typeability, an unambiguous profile was able to be established for each of the 46 isolates examined. However, 18 or 46 isolates did not encode any form of the cna gene. Although, these results suggest that most strains encode cna, it is believed that as many as 22 of 28 cna+ strains may be epidemiologically related (see below). If these 22 strains are considered as a single isolate, it is more appropriate to state that a total of 25 strains were examined, 18 of which did not encode cna. On that basis, it is doubtful that the analysis of cna will be epidemiologically useful in all cases. However, the results also suggest that cna may be an important discriminating genomic marker in at least some instances. Support for that hypothesis comes from the identification of a strain (UAMS-639) that encodes a cna gene with four B domains. The identification of this strain raises the total number of recognized cna variants to 4 (5, 13), three of which were observed during the course of this study. The possibility that *Staphylococcus aureus* may encode a cna gene with any of at least 4 easily recognizable variants supports the contention that cna Southern blots utilizing HaeIII-digested genomic DNA may offer some degree of discriminatory power despite the fact that the overall typeability with regard to cna is low.

In contrast to the results obtained with the cna probe, all 46 strains that were examined were found to encode some form of the fnbA and/or fnbB genes. When genomic DNA was digested with HaeIII and probed with 3 DNA fragments that collectively span the fnbA and fnbB genes encoded by strain S6C, a total of 11 distinguishable genotypic profiles was observed. Given the similarity in both the 5' and 3' regions of the fnbA and fnbB genes (2, 10), definitive conclusions can be drawn with respect to the presence or absence of intact copies of each gene. However, only one strain was observed (UAMS-623) with an fnbA/fnbB hybridization pattern consistent with intact forms of both genes (2, 10). Six of the 11 hybridization patterns were observed with only one strain. Other than the group that included the 22 indistinguishable isolates, the largest group that exhibited the same fnbA/fnbB hybridization profile contained a total of 9 strains. Only 5 strains could not be distinguished form the neonatal intensive care unit isolates on the basis of fnbA/fnbB hybridization profile. These results demonstrate that the fnbA/fnbB gene probes exhibit a high degree of typeability and a relatively high level of discriminatory power.

The results obtained with the hlb gene probe were very similar to those observed with the fnbA/fnbB probes. Specifically, when HindIII-digested genomic DNA was probed with DNA fragments that span the entire hlb gene and a 0.4 kbp fragment representing the region immediately upstream from hlb, a total of 11 hybridization patterns were observed, 4 of which were observed in only one strain. As with the fnbA/fnbB probes, 3 strains could not be distinguished from the neonatal intensive care unit isolates on the basis of hlb hybridization profile. However, it should be emphasized that 2 of the 3 strains that could not be distinguished on the basis of the hlb hybridization profile could be distinguished from the neonatal intensive care unit isolates on the basis of the fnbA/fnbB Southern blots. Although the largest group other than the neonatal intensive care unit isolates that exhibited the same hlb hybridization profile was limited to 4 strains, 3 groups of 4 strains that exhibited the same hlb hybridization pattern was observed. Additionally, the distinctions between hlb patterns were somewhat harder to interpret than were the distinctions observed in the fnbA/fnbB blots. For example, it was necessary to run UAMS-632 in a lane immediately adjacent to the neonatal intensive care unit isolates in order to conclusively demonstrate that 1 of the 3 fragments that hybridized with the hlb probe was distinct. Importantly, only 2 of the strains examined were not lysogenized by an hlb-converting bacteriophage.

Overall, the results of the Southern blot analysis using each of 3 probes independently revealed that both the typeability and the discriminatory power of the cna probe was lower than the fnbA/fnbB or hlb probes. While the hybridization patten observed with each of the 3 probes was identical among the 21 neonatal intensive care unit isolates that were thought to be epidemiologically related, no single probe was capable of distinguishing all of the other strains from the neonatal intensive care unit isolates. However, when all 3 probes are considered, only one strain could not be distinguished from the neonatal intensive care unit isolates.

Moreover, each of the remaining 24 strains could be clearly distinguished from the other 22 isolates. On the basis of the results presented here, it is difficult to determine whether the single strain that could not be distinguished from the neonatal intensive care unit isolates was epidemiologically related to the neonatal intensive care unit strains or represent a false identification. However, it should be noted that this strain was isolated relatively late during the course of the outbreak, which suggest that it may be indicative of the spread of the neonatal intensive care unit strain within the hospital. Overall, the independent use of all 3 gene probes offers a relatively high degree to typeability and discriminatory power.

The remaining issues to be addressed revolve around reproducibility, ease of interpretation and ease of use. With regard to reproducibility, it should be noted that this analysis included 3 pairs of internal controls. Specifically, in 3 cases, isolates were obtained from the same patient at different times or from different sites. In all 3 cases, both isolates were correctly identified as the same strain. However, in one case, a third isolate (UAMS-649) obtained from a single patient was found to type differently than the previous 2 isolates (UAMS-633 and UAMS-638). Importantly, UAMS-649 is the only strain that could not be distinguished from the 22 neonatal intensive care unit isolates. Again, this observation suggests that the isolation of UAMS-649 may be indicative of the spread of the neonatal intensive care unit strain within the hospital.

With regard to ease of interpretation, the results of this analysis were relatively straightforward in that they involve only the presence or absence of specific DNA fragments. That is particulary true with respect to the cna and fnbA/fnbB gene probes. In the case of cna, the results were exceptionally easy to enterpret in that the analysis was based only on the presence or absence of a single fragment of a clearly distinguishable size. The results of the fnbA/fnbB blots were somewhat harder to interpret in that the number of hybridizing fragments was larger and a number of fragments of similar size were observed. The resolution of these fragments would be dependent on the specific electrophoresis conditions employed. However, on the basis of overall patterns, each of the 11 hybridization patterns was clearly distinct, particularly when the results were analyzed in a single gel. The most difficult of the 3 blots to interpret was the hlb blot. That difficulty was due to the fact that, in many cases, the hybridization pattern was distinguishable only on the basis of a single fragment.

Finally, with regard to ease of use, it is relevant to note that this analysis is based on the molecular analysis of genomic DNA and does require a certain degree of technical expertise. However, the techniques involved are relatively straightforward, require little equipment that is not available in most laboratories, and are amenable to standardization between laboratories. In fact, the availability of appropriate documentation systems and analysis software could eventually lead to automation of the analysis. However, because both the technique itself and the analysis of the results would be greatly simplified if a single Southern blot could be used to attain the discriminatory power of all 3 blots, the feasibility of simultaneously using all 3 gene probes was examined.

Importantly, the present invention demonstrates that, while HaeIII digests were appropriate for the cna and fnbA/fnbB blots, the discriminatory power of the hlb blots was much higher when HindIII-digested genomic DNA was examined. Nevertheless, with one exception, the same epidemiological distinctions noted above were able to be made when HaeIII-digested genomic DNA was simultaneously hybridized with all 3 gene probes. The exception involved 8 strains that could not be definitively distinguished on the basis on the hybridization patterns observed when HaeIII-digested genomic DNA was simultaneously examined using all 3 gene probes despite the fact that the same 8 strains could be placed into 2 groups of 4 on the basis of the results obtained when HindIII-digested DNA was probed with hlb. These results demonstrate that some of the discriminatory power of the analysis is lost when HaeIII-digested DNA is simultaneously hybridized with all 3 gene probes. However, the fact that more hybridization patterns were observed when all 3 probes were used than when any single probe was used, together with the observation that all strains that were identical in the combined blot were also identical in all 3 individual blots, suggests that the simultaneous use of all 3 probes may actually increase the discriminatory power of the overall analysis.

EXAMPLE 7
An additional restriction site polymorphism in the *S. aureus* cna gene The present invention also demonstrates the finding of an additional restriction site polymorphism in the *S. aureus* cna gene and in the region immediately upstream from cna. Polymorphic sites within cna contain HincII sites within the B domain of some but not all strains. These sites are located near the Sau3a sites at 2733, 3294 and 3855 on FIG. 7. The presence of polymorphic sites in certain strains increases the discriminatory power of the techniques disclosed herein; however, detection of these polymorphisms requires the use of a different enzyme (HincII instead of HaeIII). Additionally, because the HincII sites are located within the B domains, the use of HincII eliminates much of the distinction with regard to differences in the number of B domains encoded by different strains. That is, when one uses HincII to examine strains that encode this HincII site, one can only distinguish between strains that encode one B domain and more than one B domain; one can not distinguish between strains that encode 2, 3 or 4 B domains. Therefore, while the discrimination associated with the presence or absence of these HincII sites is enhanced, some of the discrimination seen when HaeIII-digested genomic DNA is hybridized with the cna probe is lost. Thus, one must employ both kinds of digests in order to obtain an optimally enhanced level of discrimination with this probe.

The cna gene is encoded on a discrete genetic element which is inserted precisely into a single site within the chromosome. Moreover, analysis of the junction between the chromosome and the genetic element that encodes cna shows that the junctions are very close to the cna gene itself and the regions of the chromosome flanking the cna insertion site contain additional HaeIII restriction site polymorphisms.

EXAMPLE 8
Use of cna-up, pcp12, pcp and pcp34 probes

Oligonucleotide primers to cna-up used to amplify this fragment were provided by Dr. J. Patti at Texas A & M. The cna-up fragment includes the upstream junction between the cna gene and the *S. aureus* chromosome. The cna-up fragment can be used for the analysis of both cna-positive and cna-negative strains, i.e., unlike the cna probe, the cna-up probe detects a signal even in cna-negative strains.

The pcp gene was recently described by Patti et al., Gene, 1996. It is located in the region immediately downstream from the cna gene but is transcribed in the opposite direction. Primers for the amplification of the pcp gene were obtained from Dr. Patti. Primers were designed and constructed for use in the amplification of fragments representing the region between cna and pcp, i.e., pcp12 and the region upstream of pcp, i.e., pcp34. The pcp12 fragment is particularly important because it spans the downstream junction between the cna and *S. aureus* chromosome and because it can be used to detect two HaeIII restriction site polymorphisms located in the region between cna and pcp. Importantly, both of these sites are in the region that is present in both cna-positive and cna-negative strains.

The present invention discloses that there is a specific site within the *S. aureus* chromosome where the cna gene is inserted when it is present. Polymorphisms can be detected within or near this site using the methods disclosed by the present invention. In fact, using the oligonucleotide primers shown on FIG. 7, as the 5' (leftward) from the cna-up fragment and 3' (rightward) from the pcp34 fragment, a fragment can be generated that spans the entire insertion site and includes the aforementioned HaeIII sites. Thus, although many strains do not encode cna and can not be examined using a cna probe itself, probes to the cna insertion site allows a person having ordinary skill in this art to extend the cna analysis to cna-negative strains. Further, because of the HaeIII polymorphism and the fact that they occur in both cna-positive and cna-negative strains, analysis of the DNA flanking the cna insertion site provides an even more strain dependent variability.

Figure 7:
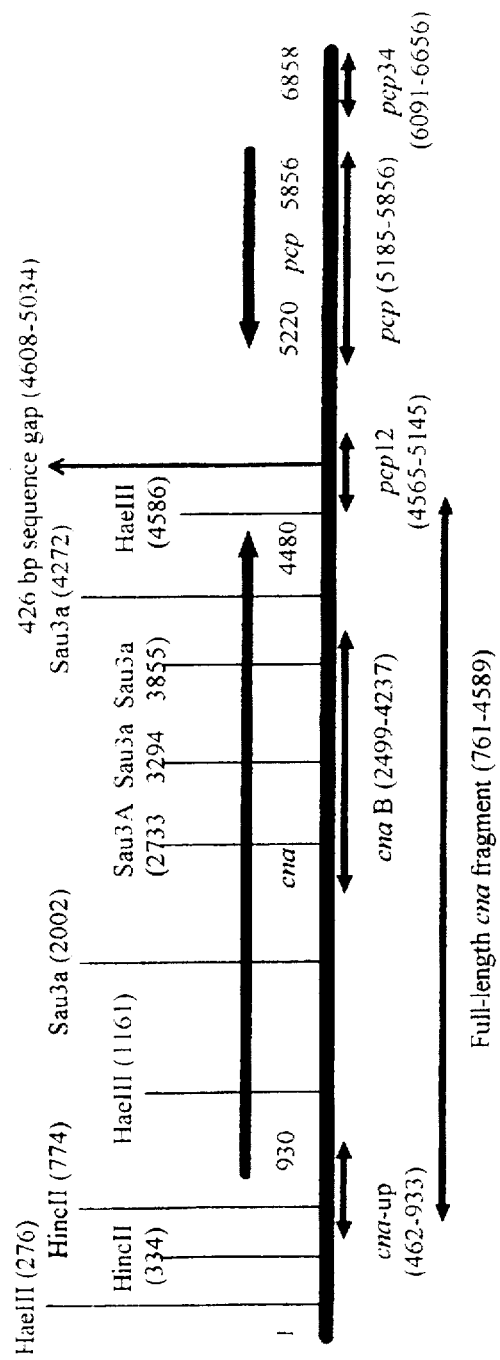
FIG. 7 depicts a graphic representation of the chromosomal region containing the cna gene. This is a graphic representation of the chromosomal region containing the cna gene. Sequence data is from strain FDA574 as described by Patti, et al. The location of the 426 bp gap in the sequence is noted by a vertical arrow. Location and direction of transcription of the cna and pcp genes are denoted by directional horizontal arrows above the bold line. Important restriction enzymes and the specific location of each restriction site are noted by vertical lines. Some strains also encode HincII sites in the B domains, the location of which is noted by the Sau 3a sites at 2733, 3294, and 3855. Strains that encode <3 B domains or 4 B domains contain a corresponding number Sau3a B domain sites. Only those Sau3a sites within or flanking the B domains are shown. DNA fragments amplified for use as probes are denoted by double-headed arrows below the bold line. Numbers in parentheses indicate terminal bases included in each fragment (i.e. the 5' and 3' bases included in the oligonucleotide primers used to amplify each fragment). Numbers not in parentheses are assigned based on the cna gene encoded by FDA574 (i.e. a strain that encodes 3 B domains). Finally, although the junctions have not been precisely defined, the DNA between the HincII site at 774 and the region near the HaeIII site at 4586 is missing in cna-negative strains.

FIG. 7 shows a graphic representation of the chromosomal region containing the cna gene. The sequence data is from strain FDA574 as described by Patti et al. The location of the 419 base pair gap in the sequence is noted by a vertical arrow. Location and direction of transcription of the cna and pcp genes are denoted by directional horizontal arrows above the bold line. Important restriction enzymes and the specific location of each restriction site are noted by vertical lines. Some strains also encode HincII sites in the B domains, the location of which is noted by the Sau3 sites at 2733, 3294 and 3855. Strains that encode less than 3 B domains or 4 B domains contain a corresponding number of Sau3a B domain sites. Only those Sau3a sites within or flanking the B domains are shown. DNA fragments amplified for use as probes are denoted by double headed arrows below the bold line. Numbers in parentheses indicate terminal bases included in each fragment i.e., the 5' and 3' bases included the oligonucleotide primers used to amplify each fragment. Numbers not in parentheses are assigned based on the cna gene encoded by FDA574, ie., a strain that encodes three B domains. Although the junctions have not been precisely defined, the DNA between the HincII site at 774 and the region near the HaeIII site at 4586 is missing in cna-negative strains.

The following references were cited herein:
1. Coleman, D., et al., Mol. Microbiol. 5:933–939, (1991).
2. Flock, J. L., et al., EMBO 6:2357, (1987).
3. Furue, M., et al., Lancet 345:1308, (1995).
4. Gillaspy, A. F., et al., Infect. Immun. 63:3373–3390, (1995).
5. Gillaspy, A. F., et al., (1995), manuscript submitted.
6. Goh, S. H., et al., J. Clin. Microbiol. 30:1642–1645, (1992).
7. Gurtler, V., et al., Microbiol. 141:1255–1265, (1995).
8. Hall, L. M., et al., Epidemiol. Infect. 103:183–192, (1989).
9. Ichiyama, S., et al., J. Clin. Microbiol. 29:2690–2695, (1991).
10. Jonsson, K., et al., Eur. J. Biochem. 202:1041–1048, (1991).
11. Mackenzie, A., et al., Diag. Microbiol. Infect. Dis. 21:69–75, (1995).
12. Mulligan, M. E., et al., Am. J. Med. 94:313–325, (1993).
13. Patti, J. M., et al., Annu. Rev. Microbiol. 48:585–617, (1994).
14. Patti, J. M., et al., J. Biol. Chem. 267:4766–4772, (1992).
15. Projan, S. J., et al., Nuc. Acid Res. 17:3305, (1989).
16. Schwarzkopf, A., et al., J. Clin. Microbiol. 32:2407–2412, (1994).
17. Sheagren, J. N., N. Engl. J. Med. 310:1368–1373, (1984).
18. Smeltzer, M. S., et al., J. Bacteriol. 174:4000–4006, (1992).
19. Smeltzer, M. S., et al., Gene 138:51–57.
20. Speziale, P., et al., J. Bacteriol. 167:77–81, (1986).
21. Tenover, F. C., et al., J. Clin. Microbiol. 32:407–415, (1994).
22. Tween, Y., et al., J. Clin. Microbiol. 29:1101–1105, (1991)
23. Van Belkum, A., et al., J. Clin. Microbiol. 33:1537–1547, (1995).
24. Waldvogel, F. A., *Staphylococcus aureus* (including toxic shock syndrome), p.1489–1510. In G. L. Mandell, R. G. Douglas, Jr., and J. E. Bennett (ed.), Principles and Practice of Infectious Diseases, 3rd ed., Churchill Livingstone, New York, (1990).

Any patents or publications mentioned in this specification are indicative of the levels of those skilled in the art to which the invention pertains. These publications are herein incorporated by reference to the same extent as if each individual publication was specifically incorporated by reference.

One skilled in the art will readily appreciate that the present invention is well adapted to carry out the objects and obtain the ends and advantages mentioned, as well as those inherent therein. The present examples along with the methods, procedures, treatments and specific compounds described herein are representative of preferred embodiments, are exemplary, and are not intended as limitations on the scope of the invention. Changes therein and other uses will occur to those skilled in the art which are encompassed within the spirit of the invention as defined by the scope of the claims.

---

What is claimed is:

1. A method of differentiating clinical isolates of *Staphylococcus aureus* in isolated genomic DNA samples, comprising the steps of:
digesting said isolated samples with a restriction enzyme:
performing Southern blot hybridization utilizing DNA probes selected from at least two of the group consisting of the cna gene, the fnbA gene, the fnbB gene, the hlb gene, the cna-up fragment, the pcp fragment, the pcp12 fragment and the pcp34 fragment to produce a hybridization profile; wherein said hybridization profile resulting from said DNA probes is capable of differentiating *Staphylococcus aureus* clinical isolates.

2. The method of claim 1, wherein said enzyme is selected from the group consisting of HaeIII and HindIII.

3. The method of claim 1, wherein genomic DNA contained in said samples is digested with both HaeIII and HindIII.

4. The method of claim 1, wherein said hybridization profiles are distinguished based on factors selected from the group consisting of the presence or absence of cna, the size of the cna gene, organization of the fnbA and fnbB genes, the presence of a lysogenic phage within hlb and the size of the restriction fragments containing the phage/bacterial DNA junction fragments.

5. The method of claim 1, wherein a hybridization profile resulting from use of probes to said cna-up fragment differentiate between isolates that are cna-positive and isolates that are cna-negative.

6. The method of claim 1, wherein a hybridization profile resulting from use of said pcp12 fragment probe detects HaeIII restriction site polymorphisms between cna and pcp.

7. The method of claim 1, wherein a hybridization profile resulting from use of said pcp12 fragment probe differentiates between isolates that are cna-positive and isolates that are cna-negative.

8. A kit for differentiating clinical isolates of *Staphylococcus aureus* in isolated samples, comprising:

(1) restriction enzymes to digest genomic DNA contained in said samples; and (2) DNA probes for at least two regions of the *Staphylococcus aureus* chromosome selected from the group consisting of the cna gene, the fnbA gene, the fnbB gene, the hlb gene, the cna-up fragment, the pcp fragment, the pcp12 fragment and the pcp34 fragment.

9. The kit of claim 8, further comprising positive controls for analyzing a hybridization profile observed in Southern blots resulting from probing with said DNA probes for said regions of the *Staphylococcus aureus* chromosome.

10. The kit of claim 8, wherein said restriction enzymes are selected from the group consisting of HaeIII and HindIII.

* * * * *